United States Patent [19]

Kissel

[11] Patent Number: 4,740,274

[45] Date of Patent: Apr. 26, 1988

[54] REFERENCE LIQUID COMPRISING CSCL

[75] Inventor: Thomas R. Kissel, Rochester, N.Y.

[73] Assignee: Eastman Kodak Company, Rochester, N.Y.

[21] Appl. No.: 900,963

[22] Filed: Aug. 29, 1986

Related U.S. Application Data

[63] Continuation of Ser. No. 773,498, Sep. 9, 1985, abandoned.

[51] Int. Cl.$^4$ .............................................. G01N 27/46
[52] U.S. Cl. .................................... 204/1 T; 204/416
[58] Field of Search .............. 204/1 B, 1 A, 416–419, 204/420; 422/55, 100

[56] References Cited

U.S. PATENT DOCUMENTS

| | | | |
|---|---|---|---|
| 4,053,381 | 10/1977 | Hamblen et al. | 204/416 |
| 4,184,936 | 1/1980 | Paul et al. | 204/416 |
| 4,214,968 | 7/1980 | Battaglia et al. | 204/418 |
| 4,271,119 | 6/1981 | Columbus | 422/50 |
| 4,302,313 | 11/1981 | Columbus | 204/418 |
| 4,544,455 | 10/1985 | Eisenhardt et al. | 204/1 T |

OTHER PUBLICATIONS

Orion Research Inc., Newsletter/Specific Electrode Technology, vol. 1, No. 4, Sep. 1969, pp. 21–23.
Scand. Journ. Clin. Lab. Invest., vol. 43, Supple. 165, pp. 43-36 (1983).
CRC Handbook of Chemistry & Physics, 65th Ed., 1984, pp. D-171 and 172.

*Primary Examiner*—T. Tung
*Attorney, Agent, or Firm*—Dana M. Schmidt

[57] ABSTRACT

There is disclosed a reference liquid for use with (a) a sample liquid to determine ionic activity of analytes, using differential analysis, and (b) two substantially identical dry-operative, ion-selective electrodes, the reference liquid comprising a solution mixture of (1) CsCl, and (2) an anion suitable for poising one of the electrodes for the analysis of the activity of $CO_2$. A method of use is also described.

3 Claims, No Drawings

REFERENCE LIQUID COMPRISING CSCL

RELATED APPLICATION

This application is a continuation application of U.S. Ser. No. 773,498 filed on Sept. 9, 1985, now abandoned.

FIELD OF THE INVENTION

This invention relates to a reference liquid used in a differential mode ion analysis requiring two substantially identical dry-operative, ion-selective electrodes.

BACKGROUND OF THE INVENTION

The ion activity measurements conducted in the assays described in U.S. Pat. No. 4,053,381, issued Oct. 11, 1977, are obtained by using a differential potential measurement on two substantially identical strips of an ion-selective electrode (hereinafter, "ISE"), responsive to a particular ion. As used herein, "dry-operative" refers to the ability of the ISE to be used within minutes, without delays for equilibration with $H_2O$. This is a property that appears to be peculiar to the ISE's described in the aforesaid patent. Aliquots of a sample, e.g., biological fluid, and a so-called "reference liquid", are both deposited. Each aliquot is deposited so that it contacts one of the two ISE's and one end of an ion bridge that allows the sample and reference solution to make liquid, and thus electrical, contact between the ends of the bridge. The voltage difference between the two electrodes is noted, and this voltage difference is converted by a calibration technique to ion concentration for that particular ion.

The reference liquid has several critical functions. For any given ion test, and therefore, for any given kind of ISE, that liquid must set a stable electrode potential (called "poising" the electrode) that is essentially constant from ISE to ISE for that type. That is, the method of calibration is set up on the assumption that such potential will be essentially constant within a manufacturing lot. A typical manufacturing lot will contain up to several hundred thousand ISE's, and the goal is for each ISE within the lot to be identical if tested with similar fluids.

In addition, it must reduce any variation in liquid junction potential when the reference liquid contacts the sample. For this reason, the reference liquid is analogous, not to calibrators, but to salt-bridge fluids such as saturated KCl, used in single or double junction reference electrodes such as the saturated calomel electrode.

Prior to this invention, commercial reference liquids for systems, such as that provided by Eastman Kodak Company for use with the Ektachem 400 ™ or 700 ™ Analyzer of Eastman Kodak Company, have been successful in most respects. However, they lacked equal ion transference that provides sufficient equal solution mobility for both the cations and anions. As a result, the ion transference at the liquid junction with the patient sample lacked the ability to swamp out, or dominate, a bias that is otherwise created when the sample ion content changes drastically (such as from patient to patient). What was observed in practice is that part of the change in the patient's ISE potential was created by a change in liquid junction potential rather than solely by a true change in ion activity. Because such changes in junction potential are not a true measure of the changed ion content, there is thus introduced a random bias. Such a bias makes proper operation difficult, since it is not amenable to correction by calibration.

For obvious reasons of simplicity, such Eastman Kodak Company reference liquid has a single composition that contains all the ions necessary for use in all the ion tests of interest, namely $K^\oplus$, $Na^\oplus$, $Cl^\ominus$ and $CO_2$. That is, it is obviously too cumbersome to switch to a different reference fluid just because a different ion is being tested in the next ISE test. Thus, a typical composition for such a conventional commercial reference liquid is a solution comprising $Na^\oplus$, $Cl^\ominus$, small amounts of $K^\oplus$ (0.0045M), acetate$^\ominus$, and $HCO_3^\ominus$, with a total ionic strength of 0.15M. The $HCO_3^\ominus$ anion is used to poise the ISE for the analysis of $CO_2$. The 0.0045M amount of $K^\oplus$ is less than conventionally considered adequate (1M) to provide equal ion solution transference.

It has also been known prior to this invention, that certain ions do provide equitransference, or sufficient equal solution mobility, such as will swamp out the junction potential noted above created by varying concentrations of the ion of choice. Thus, for the chloride anion, it has been known that the following cations have approximate equal solution mobility: potassium, ammonium, cesium and rubidium. This is apparent from the approximately equal equivalent ionic conductivity values given for these and for Cl in, e.g., pages D-171 and 172 of the CRC Handbook of Chemistry & Physics, 65th Ed., 1984.* (These have not been described, however, for use with an anion used to poise an electrode to assay for $CO_2$.) Because the commercial reference liquid included the bicarbonate anion to allow usage with the $CO_2$ ISE, it is readily evident that the ammonium cation is unacceptable in such a combination. That is, there is no pH that will keep the bicarbonate from converting into $CO_2$ gas that escapes from the liquid (which occurs at a pH $\leq 8.0$) and at the same time keeps the ammonium from converting into $NH_3$ that escapes from the liquid (at a pH $\geq 8.0$).

*$Tl^\oplus$ also is shown with sufficient solution mobility, but it is known to be unacceptable because of its toxicity and expense.

It has also been assumed prior to this invention that anions other than $Cl^\ominus$ can be used in an equitransferant salt to overcome a liquid junction potential.

SUMMARY OF THE INVENTION

This invention is based on two discoveries: first, that only $Cl^\ominus$ can be used as an equitransferant anion, and second, that of the remaining cations having equal solution mobility with chloride, only cesium is acceptable. For reasons not well understood, the use of amounts of potassium $\geq 1M$ for equal solution transference, results in unacceptable precision errors when testing for $Na^\oplus$ with the $Na^\oplus$ ISE.

More specifically, in accord with one aspect of the invention, there is provided a reference liquid for use with (a) a sample liquid to determine ionic activity of analytes, using differential analysis, and (b) two substantially identical dry-operative, ion-selective electrodes, the reference liquid comprising a solution mixture of (1) CsCl, and (2) an anion suitable for poising one of the electrodes for the analysis of the activity of $CO_2$.

In accord with another aspect of the invention, there is provided a method for determining ionic activity of analytes, using the reference liquid set forth in the previous paragraph.

Thus, it is an advantageous feature of the invention that an equitransferent reference liquid is provided that overcomes the random bias due to junction potentials created by the sample liquid, without creating imprecision when used to test for other ions such as $Na^{\oplus}$ and $HCO_3^{\ominus}$. Other advantageous features will become apparent upon reference to the following description of the preferred embodiments.

DESCRIPTION OF THE PREFERRED EMBODIMENTS

The subject invention is described in connection with a reference liquid tested with certain specific ISE's. In addition, it is useful with any ISE construction that analyzes for ions using the differential mode requiring two substantially identical dry-operative ISE's.

As noted, the preferred construction of the test element containing the ISE's is that taught in the aforesaid U.S. Pat. No. 4,053,381, the details of which are expressly incorporated herein by reference.

The reference liquid of this invention comprises a solution mixture of CsCl, and an anion that poises one of the paired ISE's for the analysis of $CO_2$. Most preferably, such poising anion is $HCO_3^{\ominus}$, in an amount of from 0.2 to 0.4M.

Regarding the Cs of the CsCl, this is used in an amount sufficient to provide equal solution transference with $Cl^{\ominus}$. Such amounts are preferably 1 to 4M, and most preferably 1 to 2M.

Optionally, the solution mixture also includes 0-0.3M $Na^{\oplus}$, 0.01M $OH^{\ominus}$, 0-0.2M $K_2SO_4$ or $Cs_2SO_4$, 0-5 g/L of a thickener such as poly(vinyl pyrrolidone), or 0-120 mg/L of a bactericide such as thiomercurisalicyclic acid available under the trade name thimerosal. In any event, such additives and composition of the reference liquid are preferably adjusted so that the pH of the reference liquid is between about 9 and 10. Below 9, the $HCO_3^{\ominus}$ tends to decompose to release $CO_2$ gas. Above 10, there is enough $OH^{\ominus}$ to possibly interfere with the carbonate in the setting of the $CO_2$ potential.

The following Table 1 lists representative useful preparations of reference liquid compositions of the invention.

TABLE 1

| Prep. No. | Useful Compositions (in M)** | | | | |
|---|---|---|---|---|---|
| | CsCl* | KHCO₃ | MHCO₃* | M'OH* | pH |
| 1 | 1.2 | — | 0.2 (Na) | 0.08 (Na) | 9.5 |
| 2 | 1.4 | — | 0.2 (Na) | 0.07 (K) | 9.5 |
| 3 | 1.2 | — | 0.2 (Na) | 0.07 (K) | 9.5 |
| 4 | 1.4 | 0.2 | — | 0.07 (Na) | 9.5 |
| 5 | 1.2 | 0.2 | — | 0.07 (Na) | 9.5 |
| 6 | 1.6 | — | 0.25 (Na) | 0.09 (K) | 9.5 |
| 7 | 1.2 | — | — | 0.005 (K) | 9.5 |
| 8 | 1.2 | — | 0.2 (Cs) | 0.08 (Na) | 9.5 |

*M or M' are noted in parentheses for each example.
**All also contained 3 g/L of poly(vinyl pyrrolidone) thickener.

For reasons that are not understood, $Rb^{\oplus}$ was found not to give improved precision compared to $K^{\oplus}$.

The method of the invention is practiced as described in the aforesaid U.S. Pat. No. 4,053,381, except using the reference liquid described above. The same reference liquid is used in all ionic analyte tests using the paired ISE format. The $Cl^{\ominus}$ ISE used to test for $Cl^{\ominus}$ analyte is the conventional Ektachem $Cl^{\ominus}$ ISE comprising silver-silver chloride layers overcoated with a polymer, such as cellulose acetate. Because the ISE's currently available are for $Na^{\oplus}$, $K^{\oplus}$, $Cl^{\ominus}$ and $HCO_3^{\ominus}$ (also described as $CO_2$), it is for these ISE's that the reference liquid must provide precision. It has been found that, when comprised as described above, the reference liquid gives the necessary precision. As noted in the following examples, precision is considered to be acceptable if the standard deviation, sigma, is $\leq 0.17$ millivolts (hereinafter mV) for Na and Cl, 0.27 for $K^{\oplus}$ and 0.35 for $CO_2$. Because of the use of significant amounts of the Cs cation and Cl anion, this reference liquid also has the necessary equal solution transference of its ions to swamp out liquid junction potentials created at the interface of the reference liquid with the sample liquid.

EXAMPLES

The following examples further illustrate the scope of the invention.

Examples 1-4: Precision When Used With a $Na^{\oplus}$ ISE

The purpose of this experiment was to determine the precision of $Na^{\oplus}$ ISE's using the reference liquid of the present invention. 48 total replicates were made for each reference liquid tested, (12 replicates each against 4 patient blood serum specimens), to determine the pooled standard deviation of the test (designated as $\sigma_m V$). The acceptable level is a pooled standard deviation no greater than 0.17 mV, a value that has been easily achieved by the commercial Kodak reference liquid already commercialized. $\sigma_m V$ was calculated using the standard formula $$\sigma_m V = \left[ \sum_{i=1}^{n} (V_i - V_m)^2/(n-1) \right]^{\frac{1}{2}} \quad (1)$$

wherein $V_i$ = individual millivolt readings for each test of 1 to n, n is the number of replicates, and $V_m$ is the mean of the values $V_i$. The ISE test elements were the $Na^+$ ISE test elements available from Eastman Kodak Company, tested on an "Ektachem 700" ™ Analyzer of Eastman Kodak by the differential method described in the aforesaid U.S. Pat. No. 4,053,381, the method details of which are expressly incorporated herein by reference.

The following reference liquids were tested:

Control = Solution containing 103.5 millimoles NaCl, 4.5 millimoles KCl, 11.5 millimoles sodium acetate, 25 millimoles NaHCO₃, about 5 g/L poly(vinyl pyrrolidone), 60 mg/L thimerasol, 0.145 millimoles of total ionic strength, and a pH of 9.0.

Example 1 = Preparation 2 above
Example 2 = Preparation 3 above
Example 3 = Preparation 4 above
Example 4 = Preparation 5 above
Comparative Example 1 = Same as Preparation 1 except that 1.4M KCl and 0.2 K₂SO₄ were used instead of 1.2M CsCl.
Comparative Example 2 = Same as Preparation 1, except that 0.2M K₂SO₄, 0.5M KCl, and 0.3M NaCl were used instead of 1.2M CsCl.

The results appear in Table 2 that follows:

TABLE 2

| Example | Equitransferent Cation of Liquid | $\sigma_m V$ |
|---|---|---|
| Control | None | 0.13 |
| 1 | Cs | 0.11 |
| 2 | Cs | 0.12* |
| 3 | Cs | 0.14 |
| 4 | Cs | 0.11 |
| Comp. Ex. 1 | K | 0.21 |

TABLE 2-continued

| Example | Equitransferent Cation of Liquid | $\sigma_{mV}$ |
| --- | --- | --- |
| Comp. Ex. 2 | K | 0.19 |

*On a subsequent repeat of this test involving 24 total replicates, $\sigma_{mV}$ was found to be 0.24. However, it is believed that this measurement was invalid because no control was run. If a control had been run and produced a $\sigma_{mV}$ of, e.g., 0.20, one could surmise that all the readings had been biased upscale by a factor, and corrections made accordingly.

This test demonstrated that $Cs^{\oplus}$, but not $K^{\oplus}$, gave a precision within the goal of $\leq 0.17$. This was particularly surprising in light of the fact that $K^{\oplus}$ would normally be the cation of choice, since one of the assays tested using the reference liquid is $K^{\oplus}$, rather than $Cs^{\oplus}$. Just why a reference liquid based upon potassium as the equitransferent cation, should produce such sodium imprecision, is not understood.

Ten separate repeats were run on the procedure of Example 1, Comparative Example 1, and the control. In all but one of those separate repeats, the use of significant, equitransferent amounts of $K^{\oplus}$ failed to provide precision ($\sigma_{mV}$) equal to or better than the control, whereas the use of $Cs^{\oplus}$ did give precision equal to or better than the control. In the one repeat that did not demonstrate this, no statistically significant difference, at the 95% confidence level, could be found between the control and $K^{\oplus}$ on the one hand, or the control and $Cs^{\oplus}$ on the other hand. The inconsistency of this one repeat is not understood, and because it was only one out of ten, it is disregarded.

Example 5: Precision When Used With a $Cl^{\ominus}$ ISE

The process of Examples 1-4 was repeated, except that the tests were of Preparation 3, on a $Cl^{\ominus}$ ISE, with 15 replicates. $\sigma_{mV}$ was found to be 0.12, well within the goal of $\leq 0.17$.

Most of the above-noted Preparations 1-6 were also tested for precision on $CO_2$ ISE's, and on $K^{\oplus}$ ISE's, in a similar manner. The standard deviations were all within the goals of 0.27 mV for $K^{\oplus}$ and 0.35 mV for $CO_2$.

Examples 6-8: Improvements in Removal of Liquid Junction Potential

To demonstrate that the reference liquid of the invention does indeed remove the liquid junction potential due to the equal solution transference of its ions, the process of Examples 1-4 was repeated, except that on the patient sample side, first 0.01M NaCl in $H_2O$, and second 0.1M NaCl in $H_2O$, were tested against the candidate reference liquids noted hereinafter. The temperature of the test was 22° C. The theoretical response, based on the Nernstian equation, for two such samples, is $$\Delta E = 58.56 \log [a_{Na}(0.1)/a_{Na}(0.01)] + \Delta E_j(0.1/0.01).$$

Solving for this equation for a zero $\Delta E_j$ (no liquid junction potential), one finds that $\Delta E$ should be 54.6 mV. The point of these examples then is to measure the actual $\Delta E$ (in mV), and determine to what extent it differs from the predicted 54.6 mV. That difference represents $\Delta E_j$. The $\Delta E$ is, of course, the difference in the electrometer reading obtained, first, when testing the 0.01M NaCl solution against candidate 1 of the following list, and second, when testing the 0.1M NaCl solution against that same candidate. The other candidate liquids were tested in the same manner.

Candidate Reference Liquids

Control = 2M KCl in $H_2O$
Ex. 6 = Preparation 1 above
Ex. 7 = Preparation 2 above
Ex. 8 = Preparation 3 above
Comparative Ex. 3 = Control for Ex. 1-4 above. (The control in this instance is the 2M KCl solution, because this is known to provide an acceptably small $\Delta E_j$—that is, it has acceptable equal solution transference in its ions.)

The results are given in the following Table 4:

TABLE 4

| Candidate Liquid | Observed $\Delta$ mV | (Observed $\Delta$ mV $-54.6$) |
| --- | --- | --- |
| Control | 55.4 | 0.80 |
| Ex. 6 | 55.2 | 0.60 |
| Ex. 7 | 55.4 | 0.80 |
| Ex. 8 | 54.7 | 0.10 |
| Comparative Ex. 3 | 61.7 | 7.10 |

As expected, Comparative Example 3 failed to provide an acceptably small $\Delta E_j$, particularly compared to what was achieved by the control and the examples of the invention. On the other hand, a variation of only $\pm 0.8$ mV from the predicted 54.6 value is acceptable.

The invention has been described in detail with particular reference to preferred embodiments thereof, but it will be understood that variations and modifications can be effected within the spirit and scope of the invention.

What is claimed is:

1. A method for determining the ionic activity of $HCO_3^{\ominus}$, $Cl^{\ominus}$, and $Na^{\oplus}$ analytes in a sample liquid, the method comprising the steps of, for said analytes,
    (a) contacting an aliquot of the sample liquid with one of two substantially identical dry operative, ion-selective electrodes and one end of an ion bridge, said electrodes including a composition selected to specifically assay for a respective one of said three analytes,
    (b) contacting an aliquot of a reference liquid with the other of said two ion-selective electrodes and the other end of said ion bridge, said reference liquid comprising a solution mixture of
        (1) CsCl, and
        (2) $HCO_3$ for poising said other electrode for the analysis of the activity of $CO_2$, and
    (c) measuring the voltage difference generated by said liquids on said electrodes,
further wherein the same reference liquid is used in Step (b) for all three tests for said three analytes.

2. A method as defined in claim 1, and further including $Na^{\oplus}$, $SO_4^{\ominus}$, $K^{\oplus}$, or $OH^{\ominus}$ in said reference liquid.

3. A method as defined in claim 1, wherein said CsCl is present in a concentration of from 1.0 to 2.0M, and said $HCO_3^{\ominus}$ is present in a concentration of from 0.2 to 0.4M.

* * * * *

UNITED STATES PATENT AND TRADEMARK OFFICE
CERTIFICATE OF CORRECTION

PATENT NO. : 4,740,274
DATED : April 26, 1988
INVENTOR(S) : Thomas R. Kissel

It is certified that error appears in the above-identified patent and that said Letters Patent are hereby corrected as shown below:

In the title, "CSCL" should read --CsCl--.

Column 2, line 12, "$K^{\oplus}$" should read --$K^{\ominus}$--.

Signed and Sealed this

Twenty-third Day of August, 1988

Attest:

DONALD J. QUIGG

Attesting Officer      Commissioner of Patents and Trademarks